US005217973A

United States Patent [19]

Bru-Magntez et al.

[11] Patent Number: 5,217,973

[45] Date of Patent: Jun. 8, 1993

[54] TRIAZOLOPYRIMIDINE DERIVATIVES WHICH ARE ANGIOTENSIN II RECEPTOR ANTAGONISTS PROCESSES FOR PREPARING THEM AND PHARMACEUTICAL COMPOSITIONS CONTAINING THEM

[75] Inventors: Nicole Bru-Magniez, Paris; Eric Nicolai, Caen; Jean-Marie Teulon, La Celle Saint Cloud, all of France

[73] Assignee: Laboratoires UPSA, Agen, France

[21] Appl. No.: 741,134

[22] Filed: Aug. 7, 1991

[30] Foreign Application Priority Data

Jul. 5, 1991 [FR] France ............................ 91 08486

[51] Int. Cl.[5] .................. A61K 31/505; C07D 487/04

[52] U.S. Cl. .................................. 514/258; 514/211; 514/217; 514/228.5; 514/233.2; 514/253; 540/544; 540/553; 540/575; 544/61; 544/118; 544/238; 544/263; 544/319; 544/326; 544/334; 548/237; 548/239; 558/414; 558/425

[58] Field of Search ........................ 544/263, 118, 61; 514/258, 233.2, 228.5

[56] References Cited

U.S. PATENT DOCUMENTS

| | | | |
|---|---|---|---|
| 4,269,980 | 5/1981 | Hardy et al. | 544/256 |
| 4,528,288 | 7/1985 | Wade | 544/263 |
| 4,532,242 | 7/1985 | Wade | 544/263 |
| 4,572,910 | 2/1986 | Wade | 544/263 |
| 4,728,652 | 3/1988 | Atwal | 544/316 |
| 5,073,566 | 12/1991 | Lifer et al. | 514/381 |

FOREIGN PATENT DOCUMENTS

| | | |
|---|---|---|
| 0152841 | 8/1985 | European Pat. Off. . |
| 859287 | 1/1961 | United Kingdom . |
| 897870 | 5/1962 | United Kingdom . |
| 951652 | 3/1964 | United Kingdom . |

OTHER PUBLICATIONS

Oikawa, Y., Sugano, K. and Yonemitsu, O.; J. Org. Chem., 1978 43 (10), 2087-2088.

Wierenga, W. and Skulnick, H. I., J. Org. Chem., 1979, 44(2), 310-311.

Houghton, R. and Lapham, D.; Synthesis, 1982 6, 451-2.

Bram, G. and Vilkas, M.; Bull, Soc. Chim. France, 1964, (5), 945-951.

Balyakina, M. V., Zhdanovich, E. S. and Preobrazhenskii, N. A.; Tr. Vses. Nauchn, Issled. Vitam in. Inst., 1961, 7, 8-16, (Chemical Abstracts, vol. 59, 11417, 1963).

Renard, M. and Maquinay, A.; Bull. Soc. Chim. Belg., 1946, 55, 98-105.

Bruce, F. W. and Coover, H. W., J. Am. Chem. Soc., 1944, 66, 2092-94.

Eby, C. J. and Hauser, C. R., J. Am. Chem. Soc., 1957, 79, 723-5.

Sung-Eun Yoo and Kyu Yang Yi; Bull. Korean. Chem. Soc., 1989 10 (1), 112.

(List continued on next page.)

*Primary Examiner*—Mukund J. Shah

*Assistant Examiner*—F. Bernhardt

*Attorney, Agent, or Firm*—Rosen, Dainow & Jacobs

[57] ABSTRACT

The present invention relates to the derivatives of formula:

Formula (I)

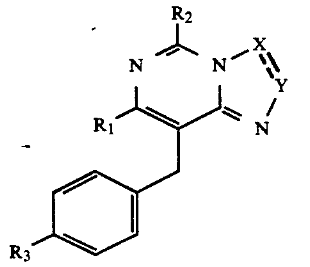

as well as to their addition salts and to their use in therapy, in particular for the treatment of cardiovascular diseases, especially for the treatment of hypertension, cardiac insufficiency and diseases of the arterial wall.

10 Claims, No Drawings

OTHER PUBLICATIONS

Durgeshwari, P. and Chaudhury, N. D.; J. Ind. Chem. Soc., 1962, 39, 735-6.
Heinz, P. and Kreglewski, A.; J. Prakt. Chem. 1963, 21 (3-4), 186-197.
Zaugg, H. E., Dunnigan, D. A., Michaels, R. J. and Swett, L. R.; J. Org. Chem., 1961, 26, 644-51.
Kagan, H. B. and Heng Suen, Y.; Bull. Soc. Chim. France, 1966 (6), 1819-22.
Rathke, M. W. and Deitch, J.; Tetrahedron Lett, 1971 (31), 2953-6.
Borries Kubel; Liebigs, Ann. Chem., 1980, 1392-1401.
Marquet, J. and Moreno-Manas, M.; Chem. Lett., 1981, 2 173-6.
Yoffe, S. T., Popov, E. M., Vatsuro, K. V. Tulikova, E. K. and Kabachnik, M. I.; Tetrahedron, 1962, 18 923-940.
Shepherd, T. M.; Chem. Ind. (London), 1970, 17 567.
Julia, M. and Chastrette, F.; Bull. Soc. Chim. France, 1962 (2), 2247.
Meyers, A. I. and Michelich, E. D.; J. Am. Chem. Soc., 1975, 97 (25) 7383.
Boots Pure Drug Co., CA:70(25):114837d (1969).
Heckles, CA:69(2):3704 (1968).
Miller, G. W. and Rose, F. L.; J. Chem. Soc., 1963, 5642-5659.
Miller, G. W. and Rose, F. L.; Chem. Soc., 1965, 3357-3368.
Miller, G. W. and Rose, F. L.; J. Chem. Soc., 1965, 3369-3372.
Brown, D. J. and Nagamatsu, T.; Aust. J. Chem. 1978(31), 2505-2515.
Brown, D. J., Grigg, G. W., Iwai, Y., Mac Andrew, K. N., Nagamatusu, T. and Van Heeswyck, R.; Aust. J. Chem., 1979(32), 2713-2726.
Konishi et al., CA96(13):103651Z (1982).
Konishi et al., CA97(7):55500W (1982).

TRIAZOLOPYRIMIDINE DERIVATIVES WHICH ARE ANGIOTENSIN II RECEPTOR ANTAGONISTS PROCESSES FOR PREPARING THEM AND PHARMACEUTICAL COMPOSITIONS CONTAINING THEM

The present invention relates to, as new products, the triazolopyrimidine derivatives of general formula (I) below and, where appropriate, to their addition salts, especially the pharmaceutically acceptable addition salts.

The compounds in question exhibit a very advantageous pharmacological profile, inasmuch as they are endowed with antagonist properties with respect to angiotensin II receptors. They are hence especially indicated for the treatment of cardiovascular diseases, especially for the treatment of hypertension, for the treatment of cardiac insufficiency and for the treatment of diseases of the arterial wall.

The present invention also relates to the process for preparing the said products and to their uses in therapy.

These triazolopyrimidine derivatives are characterised in that they correspond to the general formula (I)

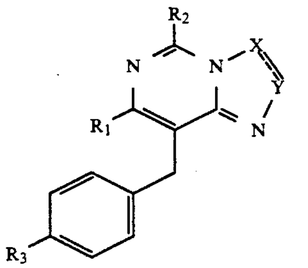

Formula (I)

In the formula (I),

- $R_1$ represents a lower alkyl radical having 1 to 6 carbon atoms or a lower alkenyl radical having 2 to 6 carbon atoms;
- $R_2$ represents a hydrogen atom, a halogen atom, a lower alkyl radical having 1 to 6 carbon atoms, a lower haloalkyl radical having 1 to 6 carbon atoms or a group $OR_5$, $SR_5$ or $NHR_5$, $R_5$ being a hydrogen atom, a lower alkyl radical having 1 to 6 carbon atoms or a $C_3$-$C_7$ cycloalkyl radical, or $NHCOR_6$, $R_6$ having the same meaning as $R_5$ but also being able to be an aromatic ring-system, a substituted or unsubstituted methane-biphenyl or a heterocycle;
- the assembly or —X⋯Y— or —Y⋯X— represents one of the following divalent radicals:

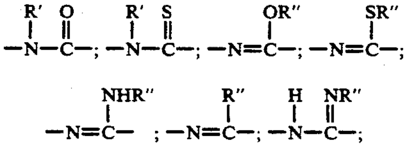

in which R′ and R″ represent:

a hydrogen atom, a lower alkyl radical having 1 to 6 carbon atoms or a $C_3$-$C_7$ cycloalkyl radical;

a group $(CH_2)_n$—CN, $(CH_2)_nCOOR_7$, $(CH_2)_n$—$OR_7$,

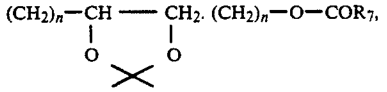

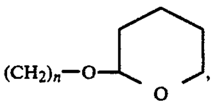

$(CH_2)_nSR_7$; n being an integer from 0 to 5 and $R_7$ a hydrogen atom or a lower alkyl radical having 1 to 6 carbon atoms;

a group $(CH_2)_pCONR_8R_9$, $(CH_2)_p$—$NR_8R_9$, p being an integer from 0 to 5, $R_8$ and $R_9$ independently representing a hydrogen atom or a lower alkyl radical having 1 to 6 carbon atoms or, with the nitrogen atom to which they are attached, being able to form a heterocycle selected form pyrrolidine, piperidine, morpholine, thiomorpholine, a phthalamide or a piperazine unsubstituted or substituted with a lower alkyl, an aromatic ring-system or a heterocycle;

a group $(CH_2)_q$—NH—$(CH_2)_r$—$COOR_{10}$, $(CH_2)_q$—NH—CO—$NHR_{11}$, $(CH_2)_q$—NH—C-S—$NHR_{11}$, q being an integer from 2 to 5 and r an integer from 0 to 5, $R_{10}$ representing a lower alkyl radical having 1 to 6 carbon atoms and $R_{11}$ representing a lower alkyl radical having 1 to 6 carbon atoms, an aromatic ring-system, a heterocycle or a group $(CH_2)_n$—$COOR_7$, n and $R_7$ being defined as above;

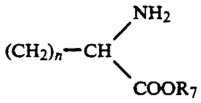 or one of its amides

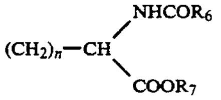

n, $R_6$ and $R_7$ being defined as above;

a radical $(CH_2)_n$-aromatic ring-system or $(CH_2)_n$-heterocycle, n being defined as above;

$R_3$ can represent a nitro or amino group or a group —$COOR_{12}$, $R_{12}$ being a hydrogen atom or a lower alkyl radical having 1 to 6 carbon atoms or a benzyl radical; $R_3$ also represents one of the following radicals:

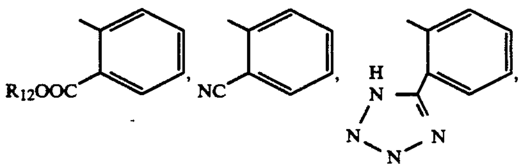

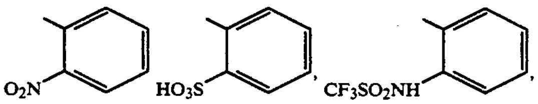

-continued

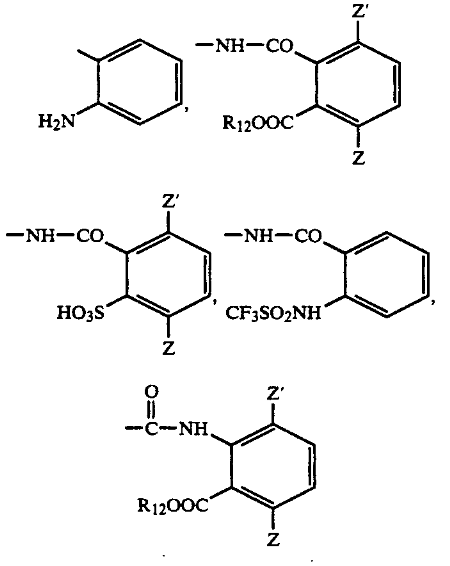

in which $R_{12}$ has the same meaning as above and Z and Z' independently represent a hydrogen atom, a lower alkyl radical, a halogen atom, a lower alkoxy radical or a trifluoromethyl radical.

The abovementioned derivatives must also be considered in their tautomeric form.

The abovementioned derivatives may take the form of addition salts, especially of pharmaceutically acceptable addition salts.

In the description and the claims, lower alkyl is understood to mean a linear or branched hydrocarbon chain having from 1 to 6 carbon atoms. A lower alkyl radical is, for example, a methyl, ethyl, propyl, isopropyl, butyl, isobutyl, tert-butyl, pentyl, isopentyl, hexyl or isohexyl radical.

Lower alkenyl is understood to mean a linear or branched hydrocarbon chain having from 2 to 6 carbon atoms and possessing an unsaturation. A lower alkenyl radical is, for example, an ethenyl, propenyl, isopropenyl, butenyl, isobutenyl, pentenyl, isopentenyl, hexenyl or isohexenyl radical.

Lower haloalkyl radical is understood to mean an alkyl radical having 1 to 6 carbon atoms, 1 to 7 hydrogen atoms of which have been substituted by 1 to 7 halogen atoms. A lower haloalkyl radical is, for example, a trifluoromethyl radical, a 2,2,2-trifluoroethyl radical, a pentafluoroethyl radical, a 2,2-difluoro-3,3,3-trifluoropropyl radical or a heptafluoropropyl radical.

$C_3$–$C_7$ cycloalkyl radical is understood to mean a saturated cyclic hydrocarbon radical; such a radical is preferably a cyclopropyl, cyclobutyl, cyclohexyl or cycloheptyl radical.

Halogen is understood to mean a chlorine, bromine, iodine or fluorine atom.

Aromatic ring-system is understood to mean a phenyl or naphthyl ring-system, optionally substituted with a lower alkyl group, a halogen, a lower haloalkyl group, a lower alkoxy, a lower thioalkyl or a nitro.

Heterocycle is understood to mean a 5- to 7-membered aromatic ring containing one to three hetero atoms such as nitrogen, oxygen or sulphur, optionally substituted with a lower alkyl radical, a halogen, a lower haloalkyl group, a lower alkoxy, a lower thioalkyl, a nitro or an aromatic ring-system.

A heterocycle is, for example, pyridine, thiophene, furan, pyrimidine, piperazine, pyridazine, a diazepine, a thiazole, an imidazole, an oxazole, a thiazepine, an oxazepine, a triazole or a tetrazole.

Lower alkoxy is understood to mean an O-(lower alkyl) group, lower alkyl being defined as above.

Lower thioalkyl is understood to mean an S-(lower alkyl) group, lower alkyl being defined as above.

According to a variant of embodiment, $R_1$ is an n-propyl group;

according to another variant of embodiment, $R_1$ is an n-butyl group;

according to a variant of embodiment, $R_2$ is a methyl group;

according to a variant of embodiment, the assembly —X⋯Y— represents one of the following divalent radicals:

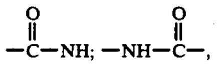

or their tautomeric form;

according to another variant of embodiment, the assembly —X⋯Y— represents the radical

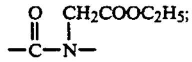

according to another variant of embodiment, the assembly —X⋯Y— represents the radical

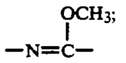

according to a variant of embodiment, $R_3$ is a 2-(5-tetrazolyl)phenyl group.

Especially preferred compounds of the invention are those which are selected from the products of formula:

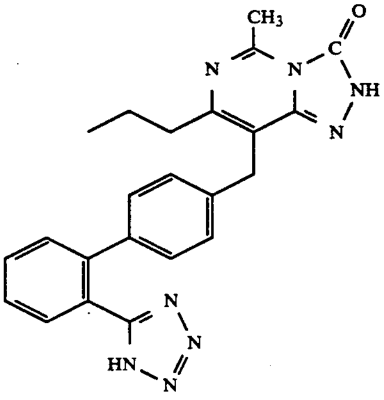

-continued

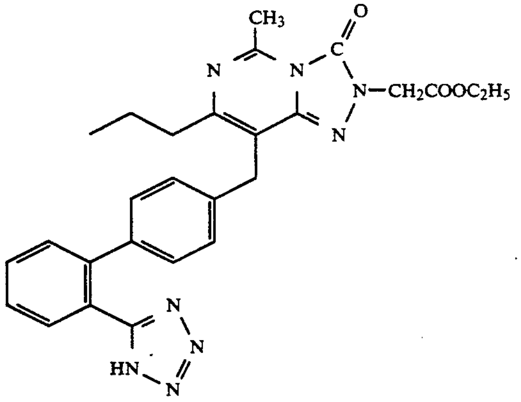

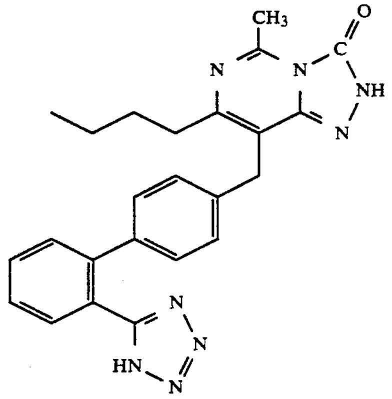

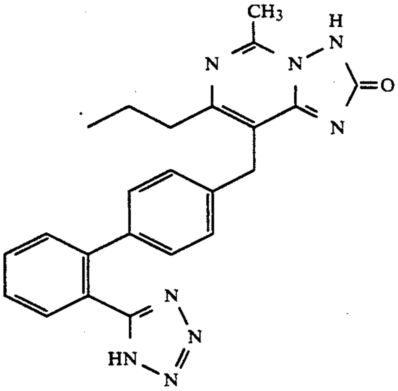

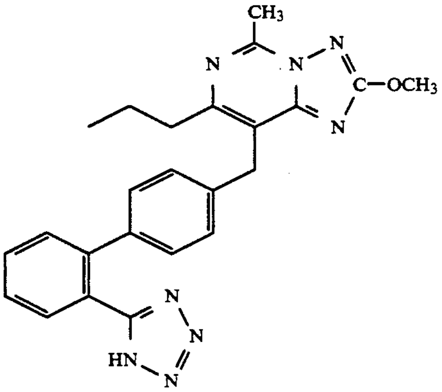

According to the invention, the compounds of formula (I) may be synthesised according to the following reaction sequence:

The alkyl 3-oxoalkanoates of formula (II):

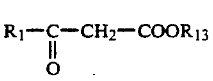

Formula (II)

in which $R_1$ is defined as above and $R_{13}$ represents a lower alkyl radical, preferably methyl or ethyl, will be prepared by methods known per se, such as, for example, the Claisen reaction or the method employing Meldrum's acid, it being possible to find these methods in the following literature references:

OIKAWA, Y. SUGANO, K. and YONEMITSU, O.; J. Org. Chem., 1978 43 (10), 2087-88.

WIERENGA, W. and SKULNICK, H. I.; J. Org. Chem., 1979, 44, 310.

HOUGHTON, R. and LAPHAM, D.; Synthesis, 1982, 6, 451-2.

BRAM, G. and VILKAS, M.; Bull. Soc. Chim. France, 1964, (5), 945-51.

BALYAKINA, M. V., ZHDANOVICH, E. S. and PREOBRAZHENSKII, N. A.; Tr. Vses. Nauchn. Issled. Vitam in. Inst., 1961, 7, 8-16.

RENARD, M. and MAQUINAY, A.; Bull. Soc. Chim. Belg., 1946, 55, 98-105.

BRUCE, F. W. and COOVER, H. W.; J. Am. Chem. Soc., 1944, 66, 2092-94.

EBY, C. J. and HAUSER, C. R.; J. Am. Chem. Soc., 1957, 79, 723-5.

By benzylation of the compounds of formula (II) with compounds of formula (III)

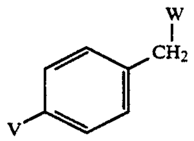

Formula (III)

in the presence of a base such as a sodium or potassium carbonate in acetone, a sodium or potassium alcoholate in an alcohol, a sodium or lithium hydride in solvents such as tetrahydrofuran, dioxane or dimethylformamide, for example, at a temperature of between 50° and 100° C., or alternatively in the presence of one equivalent of lithium chloride or bromide and two equivalents of diisopropylethylamine under reflux of tetrahydrofuran according to the reference: SUNG-EUN YOO and KYU YANG YI; Bull. Korean. Chem. Soc., 1989, 10 (1), 112, the compounds of formula:

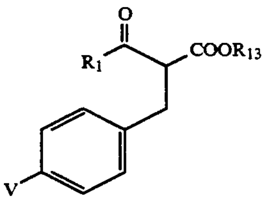

Formula (IV)

will be obtained

These compounds of formula (IV) may also be obtained by condensation of an aldehyde of formula

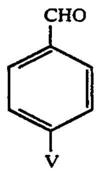

Formula (I)

with the compounds of formula (II), followed by a hydrogenation in the presence of a catalyst such as Raney nickel, palladium on charcoal or platinum oxide in a solvent such as an alcohol or tetrahydrofuran under pressure or at atmospheric pressure when the substitutions present permit it.

More generally, methods of preparation of the compounds of formula (IV) will be found in the following references:

DURGESHWARI, P. and CHAUDHURY, N. D.; J. Ind. Chem. Soc., 1962, 39, 735-6

HEINZ, P. and KREGLEWSKI, A.; J. Prakt. Chem. 1963, 21 (3-4), 186-197

ZAUGG, H. E., DUNNIGAN, D. A., MICHAELS, R. J and SWETT, L. R ; J. Org. Chem., 1961, 26, 644-51

KAGAN, H. B. and HENG SUEN, Y.; Bull. Soc. Chim. France, 1966 (6), 1819-22

RATHKE, M. W. and DEITCH, J.; Tetrahedron Lett, 1971 (31), 2953-6

BORRIES KUBEL; Liebigs Ann Chem, 1980, 1392-1401

MARQUET, J. and MORENO-MANAS, M.; Chem. Lett, 1981, 2, 173-6

IOFFE, T , POPOV, E. M., VATSURO, K. V., TULIKOVA, E. K. and KABACHNIK, M. I.; Tetrahedron, 1962, 18, 923-940

SHEPHERD, T. M.; Chem. Ind. (London), 1970, 17, 567.

In the formula (III), W represents a halogen atom, preferably chlorine or bromine.

In the same formula:

V can be a nitro group; the derivative of formula (III) is then a commercial product;

V can be a group $COOR_{15}$, $R_{15}$ being a lower alkyl or a benzyl radical; the derivative of formula (III) will then be prepared by chlorination or bromination, using N-chlorosuccinimide or N-bromosuccinimide in a solvent such as carbon tetrachloride or dibromoethane, of a p-methylbenzoic acid ester which is a commercial product, according to the reference:

JULIA, M. and CHASTRETTE, F.; Bull. Soc. Chim. France, 1962 (2), 2247; V can be a group

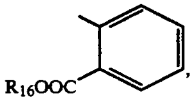

$R_{16}$ being a lower alkyl or a benzyl radical; the compounds of formula (III) are then prepared by reaction of a magnesium derivative of p-bromotoluene with a compound of formula

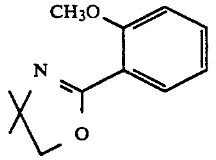

to obtain a compound of formula:

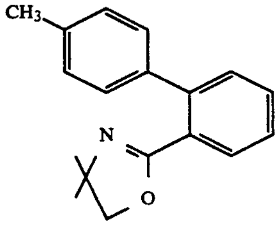

which is then hydrolysed to yield the compound of formula:

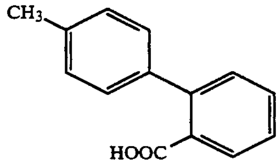

Procedures for the three steps described above will be found in the reference:

MEYERS, A. I. and MIHELICH, E. D.; J. Am. Chem. Soc., 1975, 97, 7383.

The acid is then esterified with an alcohol of formula $R_{16}OH$, $R_{16}$ being defined as above.

These derivatives are then brominated or chlorinated, for example with N-bromosuccinimide, N-chlorosuccinimide or bromine in a solvent such as carbon tetrachloride or dibromoethane or dichloroethane, to yield the compounds of formula (III) in which V is the group

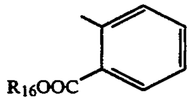

V can be the group

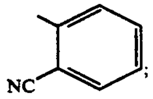

in this case, the compound:

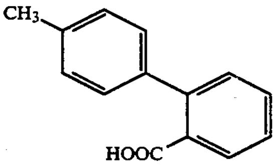

prepared above will be converted to the primary amide by the action of the acid chloride, obtained with thionyl chloride or phosphorus oxychloride, on ammonia solution, and this amide will be converted to the nitrile by the action of phosphorus oxychloride in dimethylformamide or thionyl chloride. The nitrile obtained:

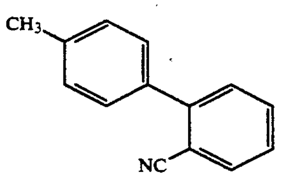

will then be brominated or chlorinated under the same conditions as the above ester to yield the compounds of formula (III) in which V is the group

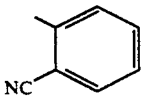

V can be the group

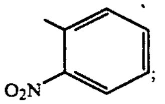

in this case, the compound

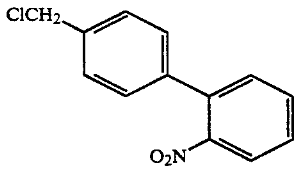

will be prepared by chloromethylation of commercial 2-nitrobiphenyl according to the references:

CA:70(25):114837 d

CA:69(2):3704

V can be a group

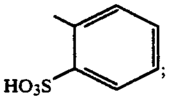

the compounds of formula (III) are then prepared in the following manner: by a Wurtz reaction between para-iodotoluene and ortho-nitroiodobenzene in the presence of copper and heating to between 180° and 210° C., the compound:

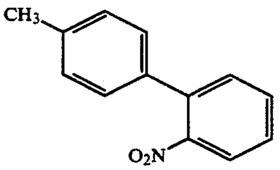

will be obtained.

After hydrogenation of the nitro group to amine and diazotisation with $NaNO_2$ in concentrated hydrochloric acid, followed by a treatment with $SO_2$ in the presence of $CuCl_2$ in acetic acid, the compound

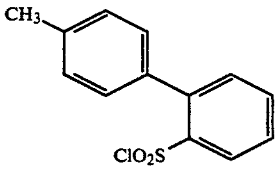

will be obtained, which compound will be treated with methanol in the presence of pyridine to yield the ester:

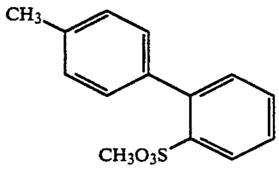

This derivative is then brominated or chlorinated, for example with N-bromosuccinimide or N-chlorosuccinimide in a solvent such as carbon tetrachloride or dibromoethane to give access to the compounds of formula (III) in which V is the group

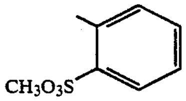

and by hydrolysis to the compounds of formula (III) in which V is the group

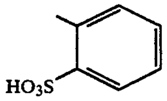

The bromination or chlorination may also be performed on the compound

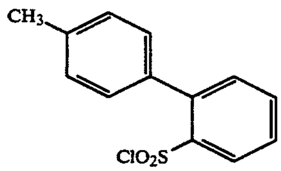

conversion to the sulphonic acid then being carried out by hydrolysis of the sulphonic acid chloride function.

In the formula (IV), $R_1$ and $R_{13}$ are defined as above and V has the same definition as in the formula (III).

In the formula (V), V has the same definition as in the formula (III), but this method of condensation will be used only when V possesses a function which is not incompatible with hydrogenation.

By the action of a compound of formula (VI)

Formula (VI)

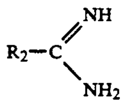

in which $R_2$ is defined as above, on the compounds of formula (IV), there will be obtained, by condensation in an alcohol in the presence of a sodium or potassium alcoholate at a temperature which can range from room temperature to the boiling point of the solvent, the compounds of formula (VII) or their tautomeric form Formula (VII)

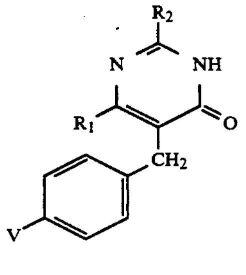

in which $R_1$, $R_2$ and V are defined as above.

By heating in $POCl_3$, for example, the derivatives of formula (VII), the derivatives of formula (VIII):

Formula (VIII)

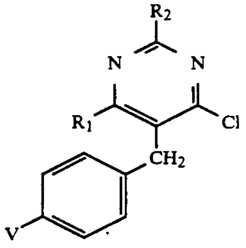

in which $R_1$, $R_2$ and V are defined as above, will be obtained.

Heating the derivatives of formula (VIII) in the presence of hydrazine or hydrazine hydrate in an alcohol under reflux will enable the derivatives of formula (IX):

Formula (IX)

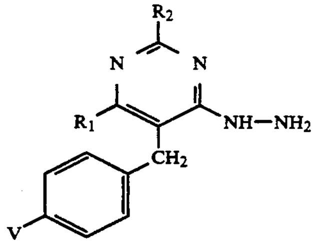

in which $R_1$, $R_2$ and V are defined as above, to be obtained.

These derivatives of formula (IX) will be cyclised by the action of carbonyldiimidazole under reflux of tetrahydrofuran, or by the action of urea by heating without a solvent or in a solvent such as N-methylpyrrolidone, or by the action of potassium xanthogenate under reflux of an alcohol such as methoxyethanol, for example, or by the action of carbon disulphide in an alcohol, for example ethanol, in the presence or absence of an amine such as triethylamine, to yield the compounds of formula (X):

Formula (X)

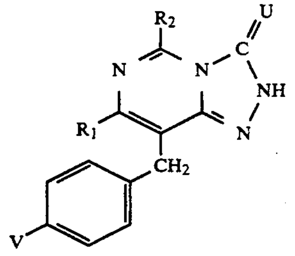

in which $R_1$, $R_2$ and V are defined as above and U represents an oxygen or sulphur atom.

The derivatives of formula (X) in which U is an oxygen atom may also be obtained directly by heating the derivatives of formula (VIII) with ethyl carbazate or methyl carbazate.

These triazolo[4,3-c]pyrimidine derivatives of formula (X) may undergo an isomerisation in a basic medium in water or in a water/alcohol mixture at a temperature of between 20° and 100° C., and optimally in the region of 60° C., it also being possible to carry out this isomerisation in an acid medium, heating in dichlorobenzene in the presence of formic acid or in acetic acid, to yield the traizolo[2,3-c]pyrimidine compounds of formula (XI):

Formula (XI)

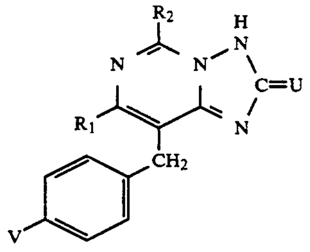

in which $R_1$, $R_2$, V and U are defined as above.

The compounds of formula (XI) in which U is a sulphur atom may also be obtained directly, by heating the derivatives of formula (XI) and carbon disulphide in pyridine or butanol under reflux.

The derivatives of formula (X) or of formula (XI) may be metalated. Depending on the conditions of metalation and the nature of the compound, the substitution will be directed towards the nitrogen atom or towards the hetero atom U. In particular, when U represents a sulphur atom, substitution will take place mainly on the S; when U represents an oxygen atom, the compounds of formula (X) will mainly yield the N-substituted derivatives, and the compounds of formula (XI) will mainly yield the O-substituted compounds. To favour N-substitution, it will be preferable to use as a metalating agent sodium hydride, lithium hydride or a sodium or potassium alcoholate in a solvent such as dimethylformamide, tetrahydrofuran or an alcohol; to favour O-substitution, sodium hydroxide, potassium hydroxide or a sodium or potassium carbonate in a solvent such as acetone or methyl ethyl ketone will be preferred as a metalating agent.

By reacting these metalated derivatives with halogenated derivatives of formula:

$$A-(CH_2)_n-CH_3$$

-continued

A—$(CH_2)_n$-aromatic

A—$(CH_2)_n$-heterocycle

A—$(CH_2)_n$—CN

A—$(CH_2)_n$—$COOR_7$

A—$(CH_2)_n$—O—$R_7$

A—$(CH_2)_n$—S—$R_7$

A—$(CH_2)_n$—$OCOR_7$

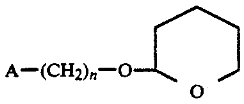

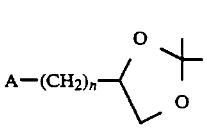

A—$(CH_2)_p$—$CONR_8R_9$

A—$(CH_2)_p$—$NR_8R_9$ in which formulae A is a halogen atom, more especially chlorine or bromine, and n, p, $R_7$, $R_8$ and $R_9$ have the same meaning as above, the derivatives substituted on the triazole ring, either on a nitrogen or via the oxygen or sulphur atom, with the groups:

—$(CH_2)_n$—$CH_3$

—$(CH_2)_n$-aromatic

—$(CH_2)_n$-heterocycle

—$(CH_2)_n$—CN

—$(CH_2)_n$—$COOR_7$

—$(CH_2)_n$—$OR_7$

—$(CH_2)_n$—$SR_7$

—$(CH_2)_n$—$OCOR_7$

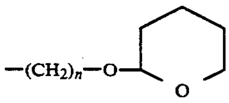

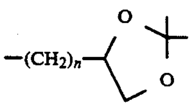

—$CH_2)_p$—$CONR_8R_9$

—$(CH_2)_p$—$NR_8R_9$ will be obtained.

The derivatives substituted on the triazole with the group —$(CH_2)_p$—$NH_2$ in the case where $R_8$ and $R_9$ are hydrogen, and which can also be obtained by catalytic hydrogenation of the derivatives substituted on the triazole with the group $(CH_2)_n$CN, may be converted by the action of a halo ester to a derivative substituted on the triazole with the group —$(CH_2)_q$—NH—$(CH_2)_r$—$COOR_{10}$, or by the action of an isothiocyanate to a derivative substituted on the triazole with the group —$(CH_2)_q$—NH—$CONHR_{11}$, or by the action of an isocyanate to a derivative substituted on the triazole with the group —$(CH_2)_q$—NH—CS—$NHR_{11}$, according to methods known to those skilled in the art.

The derivatives substituted on the triazole with the group —$(CH_2)_n$—OH, n then being greater than or equal to 2, may be converted to a derivative —$(CH_2)_n$—T, T being a halogen atom, chlorine or bromine, by the action of thionyl chloride or $PBr_3$ or hydrobromic acid, or alternatively T being a mesylate or a tosylate, obtained by the action of mesyl or tosyl chloride. Condensation of these derivatives with ethyl acetamidomalonate metalated beforehand with a sodium or potassium alcoholate under reflux of an alcohol will yield the compounds substituted on the triazole with the group

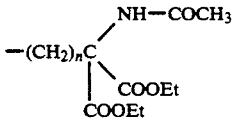

These compounds, on hydrolysis followed by decarboxylation, will enable the derivatives substituted on the triazole with amino acids

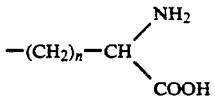

to be obtained, which derivatives may be esterified and/or converted to an amide according to methods known to those skilled in the art, for example by heating in an alcohol in the presence of thionyl chloride or by the action of an acid chloride, to yield the derivatives substituted on the triazole with the group

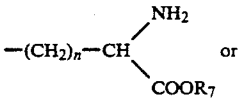

or

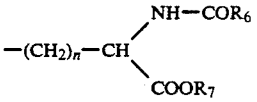

n in this case being greater than or equal to 2.

In some cases, the amine or acid functions may be protected by benzyloxycarbonyl groups for the amines or tert-butyloxy groups for the acids, and then liberated, if necessary, by hydrogenolysis or by trifluoroacetic acid treatment according to conventional methods known to those skilled in the art.

The derivatives of formula (X') or their tautomeric form

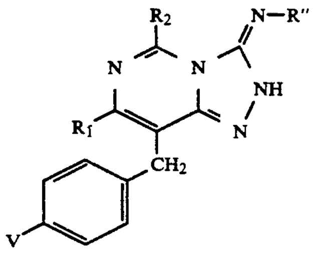

Formula (X')

in which $R_1$, $R_2$, R'' and V are defined as above, may be prepared in the following manner:

in the case where R" is a hydrogen atom, by the action of cyanogen bromide on the derivatives of formula (IX);

in the case where R" is other than a hydrogen atom, in several steps:

either by the action of an isocyanate of formula O=C=N—R", where R" is defined as above but other than a hydrogen atom, followed by a cyclisation of the urea obtained by heating with $POCl_3$, for example, or by the action of an isothiocyanate of formula S=C=N—R", where R" is defined as above but other than a hydrogen atom, followed by methylation of the thiourea obtained to S—$CH_3$ with methyl iodide and then thermal cyclisation of this thiourea derivative by heating in a suitable solvent which can be, for example, an alcohol.

The derivatives of formula (XI') or their tautomeric form:

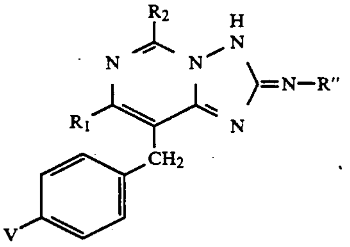

Formula (XI')

in which $R_1$, $R_2$, R" are defined as above, may be obtained via the compound of formula:

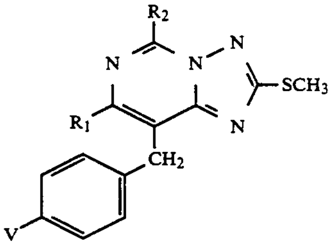

in which $R_1$, $R_2$ and V are defined as above and whose preparation has been given above, by heating in a suitable solvent such as an alcohol or dimethylformamide or N-methylpyrrolidone with a derivative of formula $H_2N$—R", in which R" is defined as above.

Moreover, the derivatives of formula (XI') may be obtained more readily by isomerisation of the compounds of formula (X') according to the isomerisation conditions described above.

The derivatives of formula (X"):

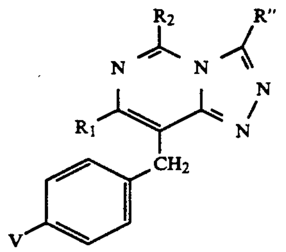

Formula (X")

in which $R_1$, $R_2$, R" and V are defined as above, may be prepared in two different ways:

either by cyclisation, by heating with an ortho ester of formula R"—C(OMe)$_3$ or R"—C(OEt)$_3$, R" being defined as above, of the hydrazinopyrimidine of formula (IX), or by cyclisatin, using $POCl_3$, of the hydrazide obtained by the action of an acid chloride of formula R"COCl or of the corresponding ester, R" being defined as above, on the hydrazinopyrimidine of formula (IX).

Isomerisation of the derivatives of formula (X") performed by heating in acetic acid will enable the triazolo[2,3-c]pyrimidine compound of formula (XI"):

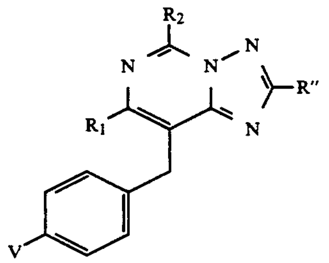

Formula (XI")

in which $R_1$, $R_2$, R" and V are defined as above, to be obtained.

More generally, some methods of preparation of triazolopyrimidines described in the following references may be used:

MILLER, G. W. and ROSE, F. L.; J. Chem. Soc., 1963, 5642-5659

MILLER, G. W. and ROSE, F. L.; J. Chem. Soc., 1965, 3357-3368

MILLER, G. W. and ROSE, F. L.; J. Chem. Soc., 1965, 3369-3372

BROWN, D. J. and NAGAMATSU, T.; Aust. J. Chem. 1978(31), 2505-2515

BROWN, D. J., GRIGG, G. W., IWAI, Y., MAC ANDREW, K. N., NAGAMATSU, T. and VAN HEESWYCK, R.; Aust. J. Chem., 1979(32), 2713-2726

MILLER, G. W. and ROSE, F. L.; Brit. Patent 951,652 of 11 Mar. 1964

MILLER, G. W. and ROSE, F. L.; Brit. Patent 859,287 of 18 Jan. 1961.

The derivatives of formula (X), (XI), (X'), (XI'), (X") and (XI") may be collectively grouped together with the derivatives substituted on a nitrogen of the triazole or substituted on the triazole via an oxygen or sulphur atom in the formula (XII):

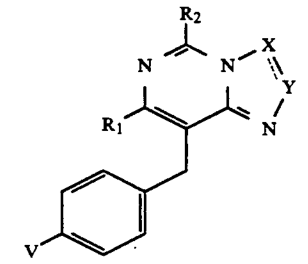

Formula (XII)

in which $R_1$, $R_2$, X, Y and V are defined as above.

The compounds of formula (XII) in which:

V is a nitro group may undergo a catalytic hydrogenation, for example in the presence of Raney nickel, in an alcohol at atmospheric pressure or under pressure, to yield the compounds of formula (XII) in which V is an amino group.

By the action of a suitably substituted phthalic anhydride on this amino derivative, the compounds of general formula (I) in which $R_3$ represents the group

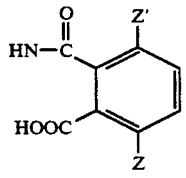

Z and Z' being defined as above, will be obtained, it being possible for the acid obtained then to be esterified to obtain the group

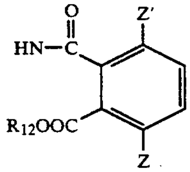

Similarly, by the action of a sulphobenzoic anhydride on these amino compounds, the compounds of general formula (I) in which $R_3$ represents the group

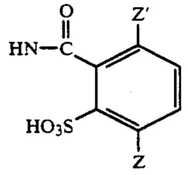

will be obtained.

Similarly, by the action of N-(trifluoromethylsulphonyl)anthranilic acid chloride, whose preparation may be found in the references:

CA96(13):103651Z

CA97(7):55500W on these amino compounds, the compounds of general formula (I) in which $R_3$ represents the group

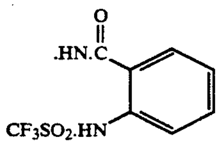

will be obtained.

The compounds of formula (XII) in which:

V is a group $—COOR_{11}$ may be hydrolysed in an acid or basic medium, or hydrogenated in the case where $R_{11}$ is a benzyl in order not to attack the other ester functions present, to yield the compounds of formula (I) in which $R_3$ is a —COOH group.

These acid derivatives may yield, after being converted to an acid chloride with thionyl chloride or to a mixed anhydride with ethyl chloroformate, by reaction with anthranilic derivatives of formula

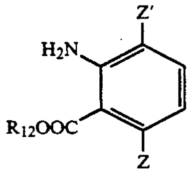

in which Z, Z' and $R_{12}$ are defined as above, the compounds of general formula (I) in which $R_3$ represents the group

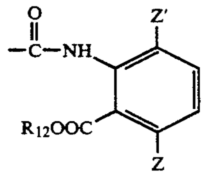

The compounds of formula (XII) in which V is the group

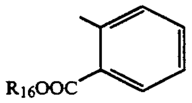

will, in the same manner, be hydrolysed, or hydrogenated in the presence of a catalyst such as palladium in the case where $R_{12}$ is a benzyl, to yield the compounds of the formula (I) in which $R_3$ is a group

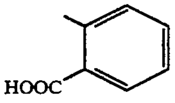

The compounds of formula (XII) in which:

V is a group

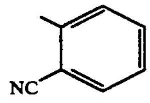

may react with one equivalent of sodium azide in a solvent such as dimethylformamide in the presence of an ammonium salt such as ammonium chloride, or by heating in toluene with trimethyltin azide followed by a treatment with gaseous hydrochloric acid in tetrahydrofuran, to yield the compounds of general formula (I) in which $R_3$ represents a group

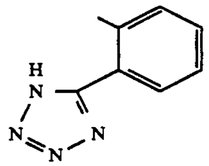

To carry out this reaction, in the case where R' or R" possesses an aliphatic alcohol function, it can be desirable to protect the latter according to methods known to those skilled in the art by an acetate or a tetrahydropyran, and then to liberate it, if necessary, after formation of the tetrazole.

The compounds of formula (XII) in which:

V is a group

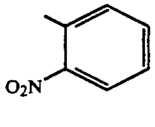

may undergo a catalytic hydrogenation, for example in the presence of Raney nickel, in an alcohol, at atmospheric pressure or under pressure, to yield compounds of general formula (I) in which $R_3$ represents a group

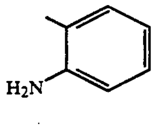

By the action of trifluoromethanesulphonic acid chloride or anhydride on these latter compounds in a solvent such as chloroform or in an aromatic solvent such as toluene in the presence of a base such as triethylamine or pyridine, or in pyridine, the compounds of general formula (I) in which $R_3$ represents a group

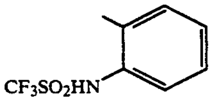

will be obtained.

Addition salts of some compounds of formula (I) may be obtained, especially pharmaceutically acceptable addition salts. There may be mentioned, in particular, when $R_2$, $R_3$ or R' or R" possess an acid function: the sodium, potassium and calcium salts, the salts of an amine such as dicyclohexylamine or those of an amino acid such as lysine. When $R_2$, $R_3$, R' or R" possess an amine function: a salt of an inorganic or organic acid, such as a hydrochloride, methanesulphonate, acetate, maleate, succinate, fumarate, sulphate, lactate or citrate.

The new compounds according to the invention possess noteworthy pharmacological properties as angiotensin II receptor antagonists, and may be used in therapy for the treatment of cardiovascular diseases, especially for treating hypertension, cardiac insufficiency and diseases of the arterial wall.

Thus, the invention encompasses pharmaceutical compositions containing as active principle the medicinal products consisting of a pharmaceutically effective amount of at least one compound of formula (I), as defined above, as well as, where appropriate, its pharmaceutically acceptable addition salts.

These compositions may be administered buccally, rectally, parenterally, transdermally or via the eye.

These compositions can be solid or liquid, and be presented in the pharmaceutical dosage forms commonly used in human medicine, such as, for example, simple or sugar-coated tablets, hard gelatin capsules, granules, suppositories, injections, transdermal systems and eye washes. They are prepared according to the methods commonly employed. The active principle, consisting of a pharmaceutically effective amount of at least one compound of the formula (I) defined as above or one of its pharmaceutically acceptable addition salts, may be incorporated therein with excipients customarily employed in these pharmaceutical compositions, such as talc, gum arabic, lactose, starch, magnesium stearate, polyvidone, cellulose derivatives, cocoa butter, semi-synthetic glycerides, aqueous or non-aqueous vehicles, fats of animal or vegetable origin, glycols, various wetting agents, dispersants or emulsifiers, silicone gels, certain polymers or copolymers, preservatives, flavourings and colourings.

The invention also covers a pharmaceutical composition having angiotensin II receptor antagonist activity, permitting, in particular, a favourable treatment of cardiovascular diseases, especially hypertension, cardiac insufficiency and diseases of the arterial wall, characterised in that it comprises a pharmaceutically effective amount of at least one compound of formula (I), mentioned above, or one of its pharmaceutically acceptable addition salts, which can be incorporated in a pharmaceutically acceptable excipient, vehicle or carrier.

The dosage varies, in particular, in accordance with the administration route, the condition being treated and the subject in question.

For example, in an adult of average weight of 60 to 70 kg, it can vary between 1 and 400 mg of active principle in one or several daily doses taken orally, or from 0.01 to 50 mg in one or several daily doses administered parenterally.

The invention also covers a process for preparing . a pharmaceutical composition, characterized in that a pharmaceutically effective amount of at least one compound of formula (I) as defined above, or one of its pharmaceutically acceptable addition salts, is incorporated in a pharmaceutically acceptable excipient, vehicle or carrier, this pharmaceutical composition being formulated in the form of hard gelatin capsules or tablets containing 1 to 400 mg of active principle or in the form of injections containing 0.01 to 50 mg of active principle.

The invention also covers a method for the therapeutic treatment of mammals, characterized in that a therapeutically effective amount of at least one compound of formula (I) as defined above, or one of its pharmaceutically acceptable addition salts, is administered to this mammal.

In animal therapy, the daily dose which can be used should normally lie between 1 and 100 mg per kg.

Other features and advantages of the invention will be more clearly understood on reading the description which follows of some examples of preparation, which are in no way limiting but given by way of illustration.

EXAMPLE 1

Ethyl 3-oxohexanoate

Formula (II): $R_1$=n-propyl $R_{13}$=ethyl 176 g of 2,2-dimethyl-4,6-dioxo-1,3-dioxane (Meldrum's acid) are dissolved in 550 ml of dichloromethane and 188 ml of pyridine. The mixture is cooled to 0° C. with a water/ice bath and 133 ml of butyryl chloride are added dropwise. When the addition is complete, the mixture is stirred for 3 hours at room temperature. The solution is washed with dilute hydrochloric acid solution, dried over magnesium sulphate and evaporated under vacuum to give an oil. This oil is dissolved in 700 ml of ethanol and the mixture is heated to reflux for 6 hours. The ethanol is evaporated off under vacuum and the residue obtained is distilled to give 145.4 g of ethyl 3-oxohexanoate in the form of a liquid of boiling point b.p.$_{20}$ 98°-100° C.

EXAMPLE 2

Ethyl 3-oxoheptanoate

Formula (II): $R_1$=n-butyl, $R_{13}$=ethyl

Prepared according to the procedure of Example 1. Liquid of boiling point b.p.$_{20}$ 115°-120° C.

EXAMPLE 3

Ethyl 2-(4-nitrobenzyl)-3-oxohexanoate

Formula (IV): $R_1$=n-propyl V=$NO_2$ $R_{13}$=ethyl 127.7 g of ethyl 3-oxohexanoate are dissolved in 700 ml of tetrahydrofuran. 174.5 g of 4-nitrobenzyl bromide and 35 g of lithium chloride are added and the mixture is stirred at room temperature. 286 ml of diisopropylethylamine are then introduced dropwise, which causes a slight exothermic effect. The mixture is then stirred for 3 hours at room temperature and thereafter for 10 hours under reflux. The solvents are evaporated off under vacuum and the residue is taken up with water and then extracted with chloroform. The organic phase is separated after settling has taken place and then washed with dilute hydrochloric acid solution, dried over magnesium sulphate and evaporated under vacuum. The oily residue obtained is taken up with isopropyl ether and the crystals formed are filtered off. The mother liquors are concentrated under vacuum and the residue is heated to 130° C. at 20 mm of mercury in order to remove the residual starting materials. 174 g of ethyl 2-(4-nitrobenzyl)-3-oxohexanoate are thereby obtained in the form of an oil, which is used without further purification for the next step.

EXAMPLE 4

Ethyl 2-[(2,-cyano-4-biphenylyl)methyl]-3-oxohexanoate

Formula (IV): $R_1$=n-propyl, $R_{13}$=ethyl

V = 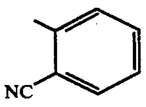

Prepared according to the procedure of Example 3, from 4'-bromomethyl-2-cyanobiphenyl.

Oil used without further purification for the . next step.

Preparation of 4'-bromomethyl-2-cyanobiphenyl:

A) 4'-Methyl-2-cyanobiphenyl 18.5 g of (4'-methyl-2-biphenylyl)carboxylic acid, prepared according to MEYERS, A. I. and MIHELICH, E. D.; J. Am. Chem. Soc., 1975, 97 (25), 7383, are heated to reflux in 60 ml of thionyl chloride for 2 hours. The thionyl chloride is concentrated under vacuum and the residue is poured into 28% ammonium hydroxide solution, the mixture is stirred for 30 minutes and the crystals obtained are drained and washed with ether and then dried to give 14.5 g of (4'-methyl-2-biphenylyl)carboxamide in the form of crystals of melting point 128° C. These crystals are taken up in 50 ml of thionyl chloride and the mixture is heated to reflux for 3 hours and then concentrated under vacuum to give 9 g of 4'-methyl-2-cyanobiphenyl in the form of crystals of melting point 45°-46° C.

B) 4'-Bromomethyl-2-cyanobiphenyl 7.9 g of 4'-methyl-2-cyanobiphenyl, prepared in A), are dissolved in 100 ml of carbon tetrachloride in the presence of 7.3 g of N-bromosuccinimide and 0.3 g of benzoyl peroxide. The mixture is heated to reflux for 6 hours and the crystals are filtered off; the remaining solution is concentrated under vacuum and the residue is crystallised in ether to give 6.6 of 4'-bromomethyl-2-cyanobiphenyl in the form of crystals of melting point 115°-118° C.

EXAMPLE 5

Ethyl 2-[(2'-cyano-4-biphenylyl)methyl]-3-oxoheptanoate

Formula (IV): $R_1$=n-butyl, $R_{13}$=ethyl,

V = 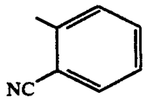

Prepared according to the procedure of Example 3. Oil used without further purification for the next step.

EXAMPLE 6

6-n-Propyl-2-methyl-4-hydroxy-5-(4-nitrobenzyl)-pyrimidine

Formula (VII): $R_1$=n-propyl, $R_2$=methyl, V=$NO_2$ 3.5 g of sodium are dissolved in 175 ml of ethanol. 9.5 g of acetamidine hydrochloride are added to this solution and the mixture is stirred for 5 minutes at room temperature. 20 g of ethyl 2-(4-nitrobenzyl)-3-oxohexanoate, prepared in Example 3, are then added and the mixture is stirred for 4 days at room temperature. The solvents are then evaporated off under vacuum and the residue is taken up with hydrochloric acid solution and extracted with ethyl acetate. The organic phase is dried over magnesium sulphate and then evaporated under vacuum to give an oily residue which crystallises in an acetone/ether mixture. The crystals are drained and dried and give 10.9 g of 6-n-propyl-2-methyl-4-hydroxy-5-(4-nitrobenzyl)pyrimidine in the form of crystals of melting point 200° C.

EXAMPLE 7

6-n-Propyl-2-methyl-4-hydroxy-5-[(2'-cyano-4-biphenylyl)methyl]pyrimidine

Formula (VII): $R_1$=n-propyl, $R_2$=methyl,

V = 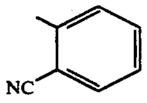

Prepared according to the procedure of Example 6. Crystals of melting point 206° C.

EXAMPLE 8

6-n-Butyl-2-methyl-4-hydroxy-5-[(2'-cyano-4-biphenylyl)methyl]pyrimidine

Formula (VII): $R_1$=n-butyl, $R_2$=methyl,

V = 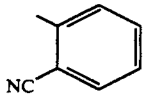

Prepared according to the procedure of Example 6. Crystals of melting point 173° C.

EXAMPLE 9

6-n-Propyl-2-methyl-5-(4-nitrobenzyl)-4-chloropyrimidine

Formula (VIII): $R_1$=n-propyl, $R_2$=methyl, V=$NO_2$ 32 g of 6-n-propyl-2-methyl-5-(4-nitrobenzyl)-4-hydroxypyrimidine, prepared in Example 6, are suspended in 45 ml of phosphorus oxychloride. The mixture is brought to reflux for 6 hours and then concentrated under vacuum. The residue is taken up with water and extracted with dichloromethane. The organic phase is washed with potassium carbonate solution, then dried over magnesium sulphate and evaporated to dryness to give 24 g of 6-n-propyl-2-methyl-5-(4-nitrobenzyl)-4-chloropyrimidine in the form of crystals of melting point 65° C.

EXAMPLE 10

6-n-Propyl-2-methyl-5-[(2'-cyano-4-biphenylyl)methyl]-4-chloropyrimidine

Formula (VIII): $R_1$=n-propyl, $R_2$=methyl,

V = 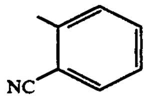

Prepared according to the procedure of Example 9. Crystals of melting point 95° C.

EXAMPLE 11

6-n-Butyl-2-methyl-4-chloro-5-[(2'-cyano-4-biphenylyl)methyl]pyrimidine

Formula (VIII): $R_1$=n-butyl, $R_2$=methyl,

V = 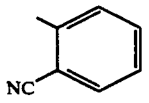

Prepared according to the procedure of Example 9. Crystals of melting point 75° C.

EXAMPLE 12

6-n-Propyl-2-methyl-4-hydrazino-5-[(2'-cyano-4-biphenylyl)methyl]pyrimidine

Formula (IX): $R_1$=n-propyl, $R_2$=methyl,

V = 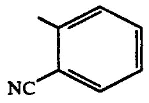

51.7 g of 6-n-propyl-2-methyl-4-chloro-5-[(2'-cyano-4-biphenylyl)methyl]pyrimidine, prepared in Example 10, are dissolved in 150 ml of ethanol and 90 ml of hydrazine hydrate. The mixture is heated to reflux for 6 hours and the solvent is concentrated to one half under vacuum and then treated with water. The crystals formed are drained, washed with water and then with ether and dried to give 46 g of 6-n-propyl-2-methyl-4-hydrazino-5-[(2'-cyano-4-biphenylyl)methyl]pyrimidine in the form of crystals of melting point 156° C.

EXAMPLE 13

6-n-Propyl-2-methyl-4-hydrazino-5-(4-nitrobenzyl)-pyrimidine

Formula (IX): $R_1$=n-propyl, $R_2$=methyl, V=$NO_2$

Prepared according to the procedure of Example 12. Crystals of melting point 126° C.

EXAMPLE 14

6-n-Butyl-2-methyl-4-hydrazino-5-[(2'-cyano4-biphenylyl)methyl]pyrimidine

Formula (IX): $R_1$=n-butyl, $R_2$=methyl,

V = 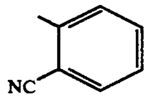

Prepared according to the procedure of Example 12. Crystals of melting point 154° C.

EXAMPLE 15

7-n-Propyl-5-methyl-8[(2'-cyano-4-biphenylyl)methyl]-triazolo[4,3-c]pyrimidin-3(2H)-one Formula (XII): $R_1$=n-propyl, $R_2$=methyl, X=CO, V = 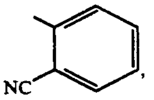 , Y=NH, X Y=single bond 33.4 g of 6-n-propyl-2-methyl-4-hydrazino-5-[(2'-cyano-4-biphenylyl)methyl]pyrimidine, prepared in Example 12, are dissolved in 600 ml of tetrahydrofuran. 15.2 g of carbonyldiimidazole are added and the mixture is heated to reflux for 1 h 30 min. The solvent is evaporated off under vacuum and the residue is taken up with water and then extracted with chloroform. The organic phase is dried over magnesium sulphate and evaporated under vacuum; the residue obtained crystallises in an ether/ethyl acetate mixture to give 26.4 g of 7-n-propyl-5-methyl-8-[(2'-cyano-4-biphenylyl)methyl]-triazolo[4,3-c]pyrimidin-3(2H)-one in the form of crystals of melting point 196° C.

EXAMPLE 16

7-n-Propyl-5-methyl-8-(4-nitrobenzyl)triazolo[4,3-c]pyrimidin-3(2H)-one

Formula (XII): $R_1$=n-propyl, $R_2$=methyl, X=CO, Y=NH, X...Y=single bond, V=$NO_2$ Prepared according to the procedure of Example 15. Crystals of melting point 225° C.

EXAMPLE 17

7-n-Butyl-5-methyl-8-[(2'-cyano-4-biphenylyl)methyl]-triazolo[4,3-c]pyrimidin-3(2H)-one Formula (XII): $R_1$=n-butyl, $R_2$=methyl, X=CO, Y=NH, X...Y=single bond, V = 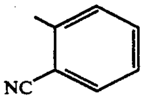

Prepared according to the procedure of Example 15. Crystals of melting point 173° C.

EXAMPLE 18

7-n-Propyl-5-methyl-8-[(2'-cyano-4-biphenylyl)methyl]triazolo[2,3-c]pyrimidin-2(3H)-one Formula (XII): $R_1$=n-propyl, $R_2$=methyl, Y=CO, X=NH, X...Y=single bond, V = 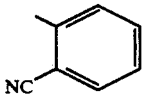

13.8 g of 7-n-propyl-5-methyl-8-[(2'-cyano-4-biphenylyl)methyl]triazolo[4,3-c]pyrimidin-3(2H)-one, prepared in Example 15, are dissolved in 40 ml of ethanol and 150 ml of 3N potassium hydroxide solution. The mixture is heated to 60° C. for 4 hours and 100 ml of water are then added. The solution is acidified with concentrated hydrochloric acid and the crystals obtained are drained, washed with water and taken up in chloroform. The chloroform solution is dried over magnesium sulphate and evaporated under vacuum. The residue obtained crystallises in an ethyl acetate/ether mixture to give 10.6 g of crystals, which are chromatographed on silica gel with a 9:1 chloroform/methanol eluent to give 8.4 g of 7-n-propyl-5-methyl-8-[(2'-cyano-4-biphenylyl)methyl]triazolo[2,3-c]-pyrimidin-2(3H)-one in the form of crystals of melting point 226° C.

EXAMPLE 19

7-n-Propyl-5-methyl-8-{[2'-(5-tetrazolyl)-4-biphenylyl]-methyl}triazolo[4,3-c]pyrimidin-3(2H)-one Formula (I): $R_1$=n-propyl, $R_2$=methyl, X=CO, Y=NH, X...Y=single bond, $R_3$ = 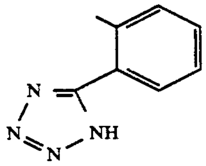

4 g of 7-n-propyl-5-methyl-8-[(2'-cyano-4-biphenylyl)methyl]triazolo[4,3-c]pyrimidin-3(2H)-one, prepared in Example 15, are dissolved in 100 ml of toluene. 2.8 g of trimethyltin azide are added and the mixture is heated to reflux for 24 hours. The crystals formed are drained in the heated state and washed with ether, then suspended in 100 ml of tetrahydrofuran. Hydrogen chloride gas is bubbled into the mixture and, after the reactants have passed completely into solution, a precipitate appears. The mixture is left overnight at room temperature and the crystals formed are drained, washed with ether and dissolved in dilute sodium hydroxide solution. This solution is washed with ether, then acidified by bubbling in sulphur dioxide and extracted with chloroform. The organic phase is dried over magnesium sulphate and evaporated under vacuum, and the residue crystallises in an ether/acetone mixture to give 1.5 g of 7-n-propyl-5-methyl-8-{[2'-(5-tetrazolyl)4-biphenylyl]methyl}triazolo[4,3-c]pyrimidin-3(2H)-one in the form of crystals of melting point 248°-249° C.

EXAMPLE 20

7-n-Propyl-5-methyl-8-{[2'-(5-tetrazolyl)-4-biphenylyl]-methyl}triazolo[2,3-c]pyrimidin-2(3H)-one Formula (I): $R_1$=n-propyl, $R_2$=methyl, X=NH, Y=CO, X...Y=single bond, $R_3$ = 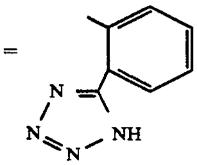

Prepared according to the procedure of Example 19. Crystals of melting point 224°-225° C.

EXAMPLE 21

Ethyl {7-n-propyl-5-methyl-8-[(2'-cyano-4-biphenylyl)methyl]-3-oxo-2,3-dihydrotriazolo[4,3-c]pyrimidin-2-yl}acetate Formula (XII): $R_1$=n-propyl, $R_2$=methyl, X=CO, Y=N $CH_2CO_2Et$, X$\cdots$Y=single bond, V = 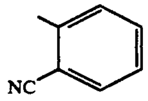

3.8 g of 7-n-propyl-5-methyl-8-[(2'-cyano-4-biphenylyl)methyl]triazolo[4,3-c]pyrimidin-3(2H)-one, prepared in Example 15, are dissolved in 50 ml of ethanol. A solution of sodium ethylate, prepared from 0.25 g of sodium in 10 ml of ethanol, is added and the mixture is stirred for 10 minutes at room temperature. 1.3 ml of ethyl bromoacetate are added and the mixture is heated to reflux for 7 hours. The solvent is concentrated under vacuum and the residue is taken up with water and extracted with ether. The organic phase is washed with cold dilute sodium hydroxide solution, then dried and evaporated under vacuum to give 4.3 g of ethyl {7-n-propyl-5-methyl-8-[(2'-cyano-4-biphenylyl)methyl]-3-oxo-2,3-dihydrotriazolo[4,3-c]pyrimidin-2-yl}acetate in the form of an oil, which is used without further purification for the next step.

EXAMPLE 22

Ethyl [7-n-propyl-5-methyl-8-{[2'-(5-tetrazolyl)-4-biphenylyl]methyl}-3-oxo-2,3-dihydrotriazolo[4,3-c]pyrimidin-2-yl]acetate Formula (I): $R_1$=n-propyl, $R_2$=methyl, X=CO, Y=N $CH_2CO_2Et$, X$\cdots$Y=single bond, $R_3$ = 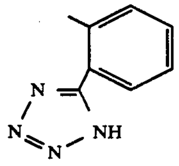

Prepared according to the procedure of Example 19. Crystals of melting point 173°-174° C.

EXAMPLE 23

2-{7-n-Propyl-5-methyl-8-[(2'-cyano-4-biphenylyl)methyl]-3-oxo-2,3-dihydro-triazolo[4,3-c]pyrimidin-2-yl}ethanol Formula (XII): $R_1$=n-propyl, $R_2$=methyl, X=CO, Y=N $CH_2CH_2OH$, X$\cdots$Y=single bond, V = 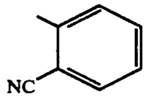

Prepared according to the procedure of Example 21, from 2-bromoethanol.

Crystals of melting point 112° C.

EXAMPLE 24

7-n-Propyl-2,5-dimethyl-8-[(2'-cyano-4-biphenylyl)methyl]triazolo[4,3-c]pyrimidin-3(2H)-one Formula (XII): $R_1$=n-propyl, $R_2$=methyl, X=CO, Y=$NCH_3$, X$\cdots$Y=single bond, V = 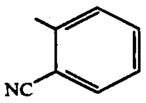

Prepared according to the procedure of Example 21, from methyl iodide.

Crystals of melting point 145° C.

EXAMPLE 25

2-[7-n-Propyl-5-methyl-8-{[2'-(5-tetrazolyl)-4-biphenylyl]methyl}-3-oxo-2,3-dihydrotriazolo[4,3-c]pyrimidin-2-yl]ethanol Formula (I): $R_1$=n-propyl, $R_2$=methyl, X=CO, Y=N $CH_2CH_2OH$, X$\cdots$Y=single bond, $R_3$ = 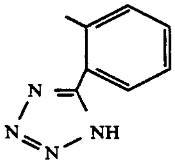

Prepared according to the procedure of Example 19. Crystals of melting point 149°-150° C.

EXAMPLE 26

7-n-Propyl-2,5-dimethyl-8-{[2'-(5-tetrazolyl)-4-biphenylyl]methyl}triazolo[4,3-c]pyrimidin-3(2H)-one Formula (I): $R_1$=n-propyl, $R_2$=methyl, X=CO, Y=$NCH_3$, X$\cdots$Y=single bond, $R_3$ = 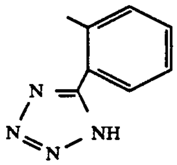

Prepared according to the procedure of Example 19. Crystals of melting point 205°-206° C.

EXAMPLE 27

7-n-Propyl-5-methyl-2-methoxy-8-[(2'-cyano-4-biphenylyl)methyl]triazolo[2,3-c]pyrimidine Formula (XII): $R_1$=n-propyl, $R_2$=methyl, X=N, Y=C—$OCH_3$, X$\cdots$Y=double bond V = 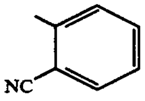

4.4 g of 7-n-propyl-5-methyl-8-[(2'-cyano-4-biphenylyl)methyl]pyrimidin-2(3H)-one, prepared in Example 18, are dissolved in 50 ml of acetone, and 2 g of potassium carbonate are added. After the addition of 2 ml of methyl iodide, the mixture is brought to reflux for 5 hours, cooled and concentrated under vacuum, then treated with water and extracted with dichloromethane. The organic phase is dried over magnesium sulphate and evaporated under vacuum, and the residue is chromatographed on silica gel in an 80:20 chloroform/acetone eluent to give 3 g of 7-n-propyl-5-methyl-2-methoxy-8-[(2'-cyano-4-biphenylyl}methyl]-triazolo[2,3-c]pyrimidine in the form of crystals of melting point 89° C.

EXAMPLE 28

7-n-Propyl-5-methyl-2-methoxy-8-{[2'-(5-tetrazolyl)-4-biphenylyl]methyl}triazolo[2,3-c]pyrimidine Formula (I): $R_1$=n-propyl, $R_2$=methyl, X=N, Y=C—$OCH_3$, X⎓Y=double bond $R_3$ =

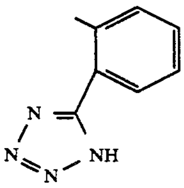

Prepared according to the procedure of Example 19. Crystals of melting point 189°-190° C.

EXAMPLE 29

7-n-Propyl-3,5-dimethyl-8-[(2'-cyano-4-biphenylyl)methyl]triazolo[2,3-c]pyrimidin-2(3H)-one Formula (XII): $R_1$=n-propyl, $R_2$=methyl, X=N—$CH_3$, Y=CO, X⎓Y=single bond,

V =

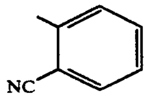

Prepared according to the procedure of Example 27 and purified by chromatography on silica gel with a 90:10 chloroform/methanol eluent.

Crystals of melting point 194° C.

EXAMPLE 30

7-n-Propyl-5-methyl-8-(4-aminobenzyl)triazolo[4,3-c]pyrimidin-3(2H)-one

Formula (XII): $R_1$=n-propyl, $R_2$=methyl, X=CO, Y=NH, X⎓Y=single bond, V=$NH_2$ 5.4 g of 7-n-propyl-5-methyl-8-(4-nitrobenzyl)-triazolo[4,3-c]pyrimidin-3(2H)-one, prepared in Example 16, are dissolved in 100 ml of methanol and hydrogenated at atmospheric pressure and room temperature in the presence of 0.8 g of Raney nickel. When the uptake of hydrogen has ceased, the catalyst is filtered off and the solvent evaporated off under vacuum to give 4.6 g of 7-n-propyl-5-methyl-8-(4-aminobenzyl)-triazolo[4,3-c]pyrimidin-3(2H)-one in the form of crystals of melting point 180° C.

EXAMPLE 31

2-[{4-[(7-n-Propyl-5-methyl-3-oxo-2,3-dihydro-triazolo[4,3-c]pyrimidin-8-yl)methyl]phenyl}aminocarbonyl]benzenesulphonic acid Formula (I): $R_1$=n-propyl, $R_2$=methyl, X=CO, Y=NH, X⎓Y=single bond, $R_3$ =

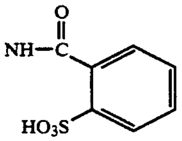

4.6 g of 7-n-propyl-5-methyl-8-(4-aminobenzyl)-triazolo[4,3-c]pyrimidin-3(2H)-one, prepared in Example 30, are dissolved in 300 ml of acetonitrile, and a solution of 2.9 g of sulphobenzoic anhydride in 30 ml of acetonitrile is added. The mixture is stirred for minutes and the crystals formed are drained and washed with ether, then dissolved in aqueous sodium bicarbonate solution. The aqueous phase is then acidified by bubbling sulphur dioxide to give 4 g of 2-[{4-[(7-n-propyl-5-methyl-3-oxo-2,3-dihydrotriazolo[4,3-c]pyrimidin-8-yl)methyl]phenyl}aminocarbonyl]benzenesulphonic acid in the form of crystals of melting point 283°-286° C.

EXAMPLE 32

Ethyl [7-n-propyl-5-methyl-8-(4-nitrobenzyl)-3-oxo-2,3-dihydrotriazolo[4,3-c]pyrimidin-2-yl]acetate Formula (XII): $R_1$=n-propyl, $R_2$=methyl, X=CO, Y=N $CH_2CO_2Et$, X⎓Y=single bond, V=$NO_2$ Prepared according to the procedure of Example 21. Crystals of melting point 144° C.

EXAMPLE 33

Ethyl [7-n-propyl-5-methyl-8-(4-aminobenzyl)-3-oxo-2,3-dihydrotriazolo[4,3-c]pyrimidin-2-yl]acetate Formula (XII): $R_1$=n-propyl, $R_2$=methyl, X=CO, Y=N $CH_2CO_2Et$, X⎓Y=single bond, V=$NH_2$ Prepared according to the procedure of Example 30. Crystals of melting point 130° C.

EXAMPLE 34

2-{[4-{[7-n-Propyl-5-methyl-2-(ethoxycarbonylmethyl)-3-oxo-2,3-dihydrotriazolo[4,3-c]pyrimidin-8-yl]methyl}phenyl]aminocarbonyl}benzenesulphonic acid Formula (I): $R_1$=n-propyl, $R_2$=methyl, X=CO, Y=N $CH_2CO_2Et$, X⎓Y=single bond, $R_3$ =

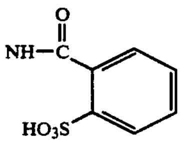

Prepared according to the procedure of Example 31. Crystals of melting point 282°-284° C.

EXAMPLE 35

2-{[4-{[7-n-Propyl-5-methyl-2-(carboxymethyl)-3-oxo-2,3-dihydrotriazolo[4,3-c]pyrimidin-8-yl]methyl}phenyl]aminocarbonyl}benzenesulphonic acid Formula (I): $R_1$=n-propyl, $R_2$=methyl, X=CO, Y=$NCH_2CO_2H$, X⋯Y=single bond,

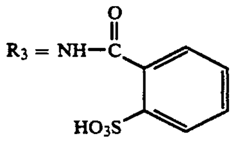

2.5 g of 2-{[4-{[7-n-propyl-5-methyl-2-(ethoxycarbonylmethyl)-3-oxo-2,3-dihydrotriazolo[4,3-c]pyrimidin-8-yl]methyl}phenyl]aminocarbonyl}benzenesulphonic acid, prepared in Example 34, are dissolved in 30 ml of water containing 1 g of sodium hydroxide. The mixture is heated to 60° C. for 2 hours, cooled and acidified with hydrochloric acid to give 2 g of 2-{[4-{[7-n-propyl-5-methyl-2-(carboxymethyl)-3-oxo-2,3-dihydrotriazolo[4,3-c]pyrimidin-8-yl]methyl}phenyl-]aminocarbonyl}benzenesulphonic acid in the form of crystals of melting point 296°-300° C.

EXAMPLE 36

7-n-Butyl-5-methyl-8-{[2'-(5-tetrazolyl)-4-biphenylyl]-methyl}triazolo[4,3-c]pyrimidin-3(2H)-one Formula (I): $R_1$=n-butyl, $R_2$=methyl, X=CO, Y=NH, X⋯Y=single bond,

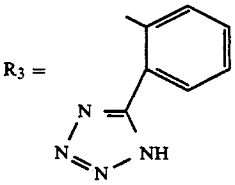

Prepared according to the procedure of Example 19. Crystals of melting point 233°-235° C.

EXAMPLE 37

7-n-Propyl-5-methyl-2-mercapto-8-(4-nitrobenzyl)-triazolo[2,3-c]pyrimidine

Formula (XII): $R_1$=n-propyl, $R_2$=methyl, X=N, Y=C—SH, X⋯Y=double bond V=$NO_2$ 3.7 g of 6-n-propyl-2-methyl-4-hydrazino-5-(4nitrobenzyl)pyrimidine, prepared in Example 13, are dissolved in 50 ml of n-butanol in the presence of 1.5 ml of carbon disulphide. The mixture is heated under reflux for 3 hours and then cooled, and the crystals obtained are drained and washed with ether and then dried to give 3.5 g of 7-n-propyl-5-methyl-2-mercapto-8-(4-nitrobenzyl)triazolo[2,3-c]pyrimidine in the form of crystals of melting point 210° C.

EXAMPLE 38

7-n-Propyl-5-methyl-2-methylmercapto-8-(4-nitrobenzyl)triazolo[2,3-c]pyrimidine

Formula (XII): $R_1$=n-propyl, $R_2$=methyl, X=N, Y=C—$SCH_3$, X⋯Y=double bond V=$NO_2$ 5 g of 7-n-propyl-5-methyl-2-mercapto-8-(4-nitrobenzyl)triazolo[2,3-c]pyrimidine, prepared in Example 37, are dissolved in 50 ml of chloroform and 2.2 ml of triethylamine. 1.5 ml of methyl iodide are added and the mixture is stirred at room temperature for hours and then left overnight. The mixture is then washed with dilute sodium hydroxide solution and the organic phase is separated after settling has taken place, dried over magnesium sulphate and evaporated under vacuum to give a residue which crystallises in an ether/pentane mixture to yield 4 g of 7-n-propyl-5-methyl-2-methylmercapto-8-(4-nitrobenzyl)triazolo[2,3-c]pyrimidine in the form of crystals of melting point 130° C.

EXAMPLE 39

7-n-Propyl-5-methyl-2-methylmercapto-8-(4-aminobenzyl)triazolo[2,3-c]pyrimidine

Formula (XII): $R_1$=n-propyl, $R_2$=methyl, X=N, Y=C—$SCH_3$, X⋯Y=double bond V=$NO_2$ Prepared according to the procedure of Example 30. Oil used without further purification for the next step.

EXAMPLE 40

2-[{4-[(7-n-Propyl-5-methyl-2-methylmercapto-triazolo[2,3-c]pyrimidin-8-yl)methyl]phenyl}aminocarbonyl]benzenesulphonic acid Formula (I): $R_1$=n-propyl, $R_2$=methyl, X=N, Y=C—$SCH_3$, X⋯Y=double bond

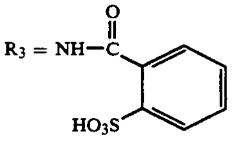

Prepared according to the procedure of Example 31.

Crystals of melting point 250°-252° C.

EXAMPLE 41

7-n-Propyl-5-methyl-2-mercapto-8-[(2'-cyano-4-biphenylyl)methyl]triazolo[2,3-c]pyrimidine Formula (XII): $R_1$=n-propyl, $R_2$=methyl, X=N, Y=C—SH, X⋯Y=double bond

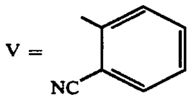

Prepared according to the procedure of Example 37. Crystals of melting point 202° C.

EXAMPLE 42

7-n-Propyl-5-methyl-2-mercapto-8-{[2'-(5-tetrazolyl)-4-biphenylyl]methyl}triazolo[2,3-c]pyrimidine Formula (I): $R_1$=n-propyl, $R_2$=methyl, X=N, Y=C—SH, X⎓Y=double bond $R_3$ = 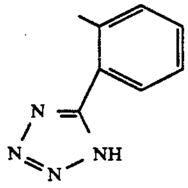

Prepared according the procedure of Example 19.

EXAMPLE 43

Ethyl {7-n-propyl-5-methyl-8-[(2'-cyano-4-biphenylyl)methyl]triazolo[2,3-c]pyrimidin2-yl}mercaptoacetate Formula (XII): $R_1$=n-propyl, $R_2$=methyl, X=N, Y=C—$SH_2$—$CO_2$—Et, X⎓Y=double bond V = 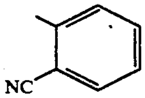

4 g of 7-n-propyl-5-methyl-8-[(2'-cyano-4-biphenylyl)methyl]2-mercaptotriazolo[2,3-c]pyrimidine, prepared in Example 41 are dissolved in 40 ml of ethanol, and a solution of sodium ethylate, obtained by adding 0.3 g of sodium to 5 ml of ethanol, is added. The mixture is stirred for 10 minutes at room temperature, and 1.5 ml of ethyl bromoacetate are added. The mixture is then brought to reflux for 2 hours, the solvent is thereafter evaporated under vacuum and the residue is taken up with water and extracted with ethyl acetate. The organic phase is dried over magnesium sulphate and evaporated under vacuum, and the residue obtained crystallises in an ether/pentane mixture to give 2.9 g of ethyl {7-n-propyl-5-methyl-8-[(2'-cyano-4 -biphenylyl)-methyl]triazolo[2,3-c]pyrimidin-2-yl}mercaptoacetate in the form of crystals of melting point 103° C.

EXAMPLE 44

Ethyl [7-n-propyl-5-methyl-8-{[2'-(5-tetrazolyl)-4-biphenylyl]methyl}triazolo[2,3-c]pyrimidin-2-yl]mercaptoacetate Formula (I): $R_1$=n-propyl, $R_2$=methyl, X=N, Y=C—$SCH_2$—$CO_2$—Et, X⎓Y=double bond $R_3$ = 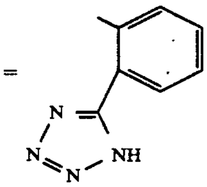

Prepared according to the procedure of Example 19. Crystals of melting point 127°–8° C.

PHARMACOLOGY

I. Principle

The affinity of the products of the examples for angiotensin II receptors is assessed by a technique of displacement of a radiolabelled ligand specifically bound to the adrenal angiotensin II receptors in the rat.

II. Procedure

An aliquot of a rat adrenal gland homogenate is incubated in the presence of a single concentration of [$^{125}$I]-SIAII(Sar$^1$, Tyr$^4$, Ile$^8$-angiotensin II) which is an angiotensin II receptor antagonist, and two concentrations of competitive agents ($10^{-5}$M, $10^{-7}$M) for 60 min at 25° C.

The reaction is stopped by adding buffer, followed by rapid filtration through glass-paper filters. The nonspecific binding is determined in the presence of angiotensin II.

III. Expression of the Results

The results are expressed, for the concentrations tested, as a percentage displacement of the radiolabelled ligand specifically bound to the adrenal angiotensin II receptors.

IV. Results

| Product of example | Percentage displacement of the labelled ligand | |
|---|---|---|
| | lE-7M | lE-5M |
| Example 19 | 48 | 66 |
| Example 20 | 45 | 61 |
| Example 22 | 57 | 68 |
| Example 31 | 54 | 81 |
| Example 34 | 52 | 80 |
| Example 35 | 21 | 67 |

TOXICOLOGY

The products of the examples described exhibit excellent tolerability after oral administration.

Their median lethan dose in the rate was assessed as being greater than 300 mg/kg.

CONCLUSION

The products of the examples described exhibit a good affinity for angiotensin II receptors. On this basis, they may be used beneficially in the various pathologies in which angiotensin II is involved, especially in the treatment of arterial hypertension, cardiac insufficiency and diseases of the arterial wall, at dosages of 1 to 400 mg taken orally and 0.01 to 50 mg administered intravenously, in one or several doses per day.

We claim:

1. Triazolopyrimidine compounds of formula (I)

Formula (I)

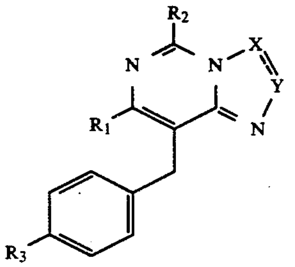

in which:

$R_1$ is a lower alkyl radical having 1 to 6 carbon atoms;

$R_2$ is a hydrogen atom, or a lower alkyl radical having 1 to 6 carbon atoms;

the assembly —X⋯Y— or —Y⋯X— represents one of the following divalent radicals:

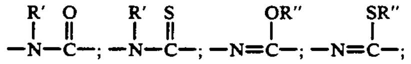

in which R' and R" represent:

a hydrogen atom, a lower alkyl radical having 1 to 6 carbon atoms or a $C_3$-$C_7$ cycloalkyl radical;

a group $-(CH_2)_nCOOR_7$ or $-(CH_2)_{n'}-OR_7$ in which n is an integer from 0 to 5, n' is an integer from 1 to 5, $R_7$ is the hydrogen atom or a lower alkyl radical having 1 to 6 carbon atoms;

$R_3$ represents $NO_2$; $NH_2$;

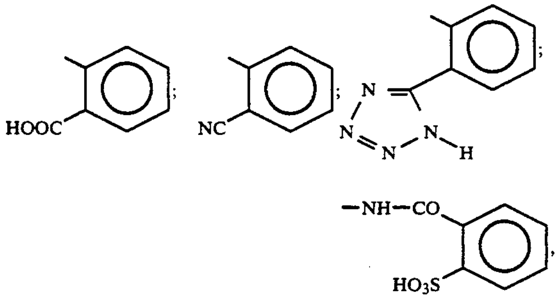

as well as their tautomeric forms and their addition salts.

2. Compounds according to claim 1, wherein $R_1$ is a group selected from n-propyl and n-butyl.

3. Compounds according to claim 1, wherein $R_2$ is a methyl group.

4. Compounds according to claim 1, wherein the assembly —X⋯Y— represents one of the following divalent radicals:

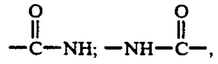

or their tautomeric form.

5. Compounds according to claim 1, wherein the assembly —X⋯Y— represents the radical:

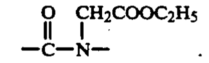

6. Compounds according to claim 1, wherein the assembly —X⋯Y— represents the radical:

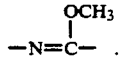

7. Compounds according to claim 1 wherein $R_3$ is a 2-(5-tetrazolyl)phenyl group.

8. Compounds according to claim 1, wherein they are selected from the compounds of formula:

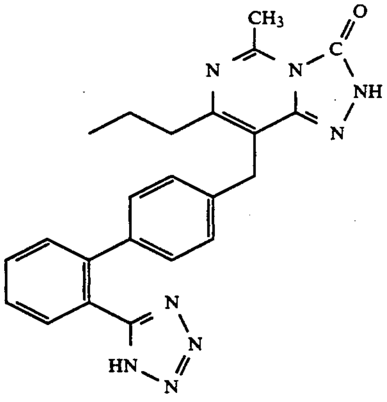

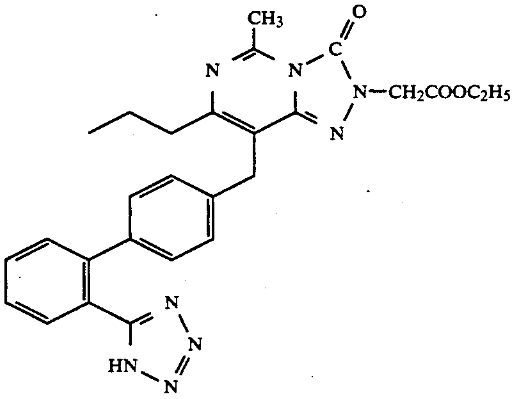

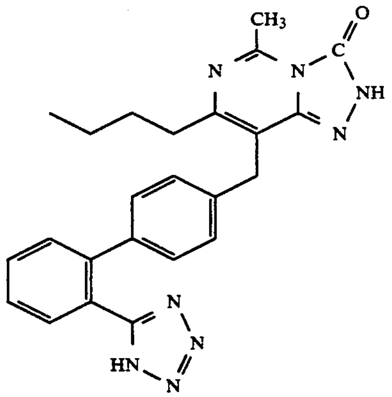

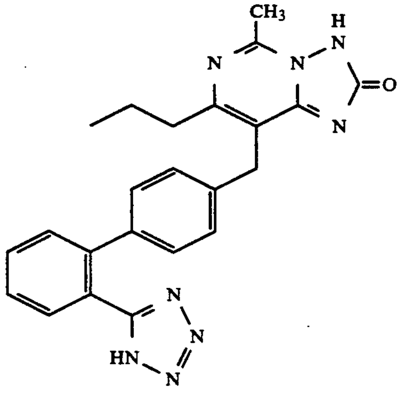

-continued

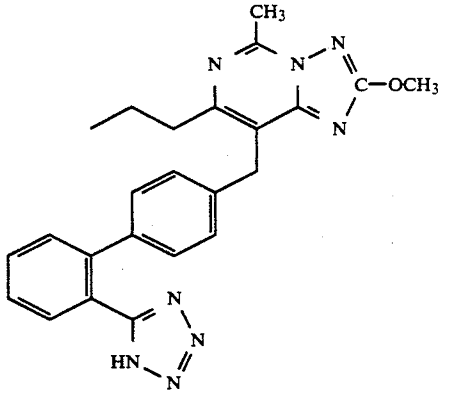

9. Triazolopyrimidine compounds of formula (I)

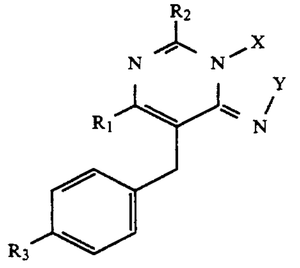

in which:

$R_1$ is n-propyl or n-butyl;

$R_2$ is methyl;

the assembly —X....Y— or —Y....X— represents one of the following divalent radicals:

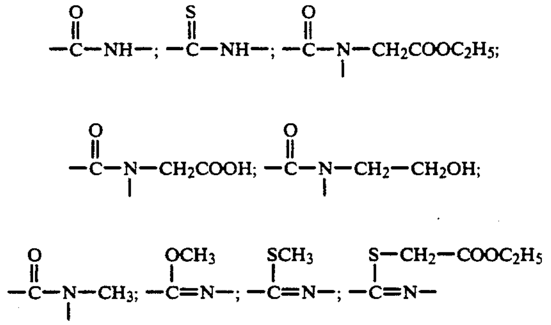

R3 represents $NO_2$; $NH_2$;

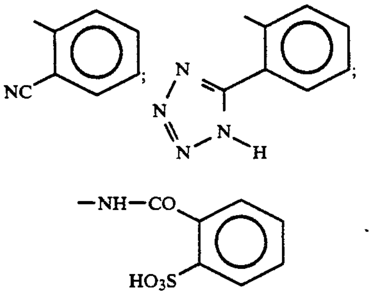

as well as their tautomeric forms and their addition salts.

10. Pharmaceutical composition, characterised in that it comprises a pharmaceutically effective amount of at least one compound of formula (I) as defined in claim 1, or one of its pharmaceutically acceptable addition salts, incorporated in a pharmaceutically acceptable excipient, vehicle or carrier.

* * * * *